(12) United States Patent
Knipe et al.

(10) Patent No.: US 11,111,468 B2
(45) Date of Patent: Sep. 7, 2021

(54) ELECTROMETHANOGENESIS REACTOR

(71) Applicant: LAWRENCE LIVERMORE NATIONAL SECURITY, LLC, Livermore, CA (US)

(72) Inventors: Jennifer Marie Knipe, Oakland, CA (US); Sarah E. Baker, Dublin, CA (US); Marcus A. Worsley, Hayward, CA (US); Swetha Chandrasekaran, Dublin, CA (US)

(73) Assignee: Lawrence Livermore National Laboratory, LLC, Livermore, CA (US)

( * ) Notice: Subject to any disclaimer, the term of this patent is extended or adjusted under 35 U.S.C. 154(b) by 612 days.

(21) Appl. No.: 15/949,378

(22) Filed: Apr. 10, 2018

(65) Prior Publication Data

US 2019/0309242 A1 Oct. 10, 2019

(51) Int. Cl.
| | |
|---|---|
| *C12M 1/107* | (2006.01) |
| *C12M 1/42* | (2006.01) |
| *C12P 5/02* | (2006.01) |
| *C12M 1/00* | (2006.01) |
| *C12N 13/00* | (2006.01) |

(52) U.S. Cl.
CPC ............ *C12M 21/04* (2013.01); *C12M 23/34* (2013.01); *C12M 35/02* (2013.01); *C12P 5/023* (2013.01); *C12N 13/00* (2013.01)

(58) Field of Classification Search
CPC ...... C12M 21/04; C12M 23/34; C12M 35/02; C12P 5/023; C12N 13/00
See application file for complete search history.

(56) References Cited

U.S. PATENT DOCUMENTS

| | | | |
|---|---|---|---|
| 8,440,438 B2 | 5/2013 | Cheng et al. | |
| 2011/0165667 A1* | 7/2011 | Mets .................. | C25B 3/04 |
| | | | 435/297.1 |
| 2017/0335473 A1* | 11/2017 | Armiger ........ | C12Y 101/01001 |

OTHER PUBLICATIONS

Campbell, et. al. "Membrane/Mediator-Free Rechargeable Enzymatic Biofuel Cell Utilizing Graphene/Single Wall Carbon Nanotube Cogel Electrodes" ACS Appl. Mater. Interfaces 2015, 7, 4056-4065 (Year: 2015).*
Mao, et. al. "Graphene aerogels for efficient energy storage and conversion" Energy Environ. Sci. 2018, 11, 772-799 (Year: 2018).*

(Continued)

*Primary Examiner* — William H. Beisner
*Assistant Examiner* — Danielle B Henkel
(74) *Attorney, Agent, or Firm* — Eddie E. Scott

(57) ABSTRACT

Generation of energy and storage of energy for subsequent use is provided by electromethanogenesis of carbon dioxide into a fuel gas and the storage of the fuel gas for subsequent use. An electromethanogenic reactor includes an anode conductor and a cathode conductor wherein the cathode conductor includes submicron to micron scale pores. Electromethanogenesis microbes and/or enzymes are located in the micron scale pores of the cathode electrode conductor. Carbon dioxide is introduced into the electromethanogenic reactor and the electromethanogenesis microbes/enzymes and the carbon dioxide interact and produce a fuel gas. The fuel gas is stored for subsequent use, for example use in power generation.

14 Claims, 13 Drawing Sheets

(56) References Cited

OTHER PUBLICATIONS

Marie et al "Platinum supported on resorcinol-formaldehyde based carbon aerogels for PEMFC electrodes: Influence of the carbon support on electrocatalytic properties" Journal of App. Electrochem. (2007) 37:147-153 (Year: 2006).*
Deutzmann et al., "Extracellular Enzymes Facilitate Electron Uptake in Biocorrosion and Bioelecrosynthesis," mbio, vol. 6, No. 2, 2015, pp. 1-8.
Hara et al., "Mechanism of Electromethanogenic Reduction of Co2," Energy Procedia, 37, 2013, pp. 7021-7028.

* cited by examiner

ELECTROMETHANOGENESIS REACTOR

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present application relates to electromethanogenesis and more particularly to a electromethanogenesis reactor.

State of Technology

This section provides background information related to the present disclosure which is not necessarily prior art.

Electromethanogenesis is a form of electrofuel production where methane is produced by direct biological conversion from electrical current and carbon dioxide. Electromethanogenesis uses microbes adsorbed on planar graphite electrodes. The current density and consequently the volumetric productivity of this design are limited by the electrode interfacial area that is accessible to the microbes. Additionally, it is difficult to maintain the reactor geometry and density when scaling up of these electrode materials to large reactor sizes.

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

We are entering an era where energy from photovoltaics, wind, and other renewable sources is abundant and inexpensive during peak production periods. Technologies that can store this energy long term (e.g. seasonally) are highly desired. Storage as methane would allow Methane to serve as an energy storage medium that can be stored or transported using mature technologies and immediately integrated into existing infrastructure. Natural gas power plants emit fewer pollutants and are more efficient than coal-fired power plants. Furthermore, for each methane molecule produced, a $CO_2$ molecule is consumed, reducing the climate impacts of burning natural gas. Electromethanogenesis is the microbial conversion of $CO_2$ to methane and has the potential to be less capital and energy intensive than chemical methods for this conversion (electrolysis followed by Sabetier process). However, to capitalize on the efficiency of microbes, new reactor designs and electrode materials are needed to increase current density and scalability.

The inventors' apparatus, systems, and methods provide the generation of energy and the storing of the energy for subsequent use by providing carbon dioxide, electromethanogenesis of the carbon dioxide into a fuel gas, and the storing of the fuel gas for subsequent use. The inventors' apparatus, systems, and methods utilize an electromethanogenic reactor having an anode conductor and a cathode conductor wherein the cathode conductor includes nanometer to micron scale pores. Electromethanogenesis microbes or enzymes are located in the micron scale pores of the cathode electrode conductor. Carbon dioxide is introduced into the electromethanogenic reactor, wherein the electromethanogenesis microbes or enzymes and the carbon dioxide interact and produce a fuel gas. The fuel gas is stored for subsequent use, for example use in power generation.

The inventors' apparatus, systems, and methods provide a scalable, production module for microbial methanogenesis of methane gas from $CO_2$. This inventors' apparatus, systems, and methods may also be used in other microbial electrosynthesis including production of other fuels or specialty chemicals, such as hydrogen peroxide or acetate, from $CO_2$. The inventors' apparatus, systems, and methods utilize 3D printed electrode materials with adsorbed electromethanogenesis microbes or enzymes that have tunable geometry, surface area, and surface chemistry to maximize current density in microbial electromethanogenesis of $CO_2$ to methane in a modular reactor. Volumetric productivity scales with current density, therefore by tuning the surface area and microbe/enzyme adsorption the current density can be optimized. The inventors' apparatus, systems, and methods have use in energy storage, $CO_2$ mitigation, industrial biogas production, fuel synthesis, syngas, and other applications.

The inventors' apparatus, systems, and methods use 3D printed high surface area electrode-based reactors with adsorbed microbes/enzymes for charge transfer to overcome the limitations of microbial electromethanogenesis. The inventors' apparatus, systems, and methods have numerous benefits that include three unique aspects that are designed to increase charge transfer efficiency and reactor volumetric productivity:

Aspect #1—This is the first use of graphene aerogels for microbial electromethanogenesis, which allows the current density to be maximized due to the ability to control material pore size (and thus biologically accessible surface area) over 4 orders of magnitude (1 nm to 10 μm) and conductivity from 1 to 100's of S/cm.

Aspect #2—The inventors' apparatus, systems, and methods use adsorbed enzymes to mediate charge transfer rather than whole microbial cultures. The use of enzymes to mediate charge transfer can increase current density, since nanometer scale enzymes can access more electrode surface area than significantly larger micron scale whole microbes. Furthermore, using enzymes rather than microbes for the critical charge transfer step allows a wider range of process conditions, e.g. temperatures and pH, which can be used to increase catalytic activity and $CO_2$ solubility. Separating the charge transfer from the methanogenesis step to a chemical intermediate production step also allows a wider range of microbial species that can be used for methanogenesis; processes for microbial methane production from syngas have been optimized and established for industrial biogas production.

Aspect #3-3D printing these reactors maximizes volumetric productivity by both optimally utilizing 3D space and reducing diffusion limitations. Furthermore, 3D printed reactors allow for modular and flow-through designs, positioning the technology for scale-up and commercialization.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

FIG. 2I illustrates details of the 3D printed cathode electrode with adsorbed enzymes.

DETAILED DESCRIPTION OF SPECIFIC EMBODIMENTS

Figure 1:
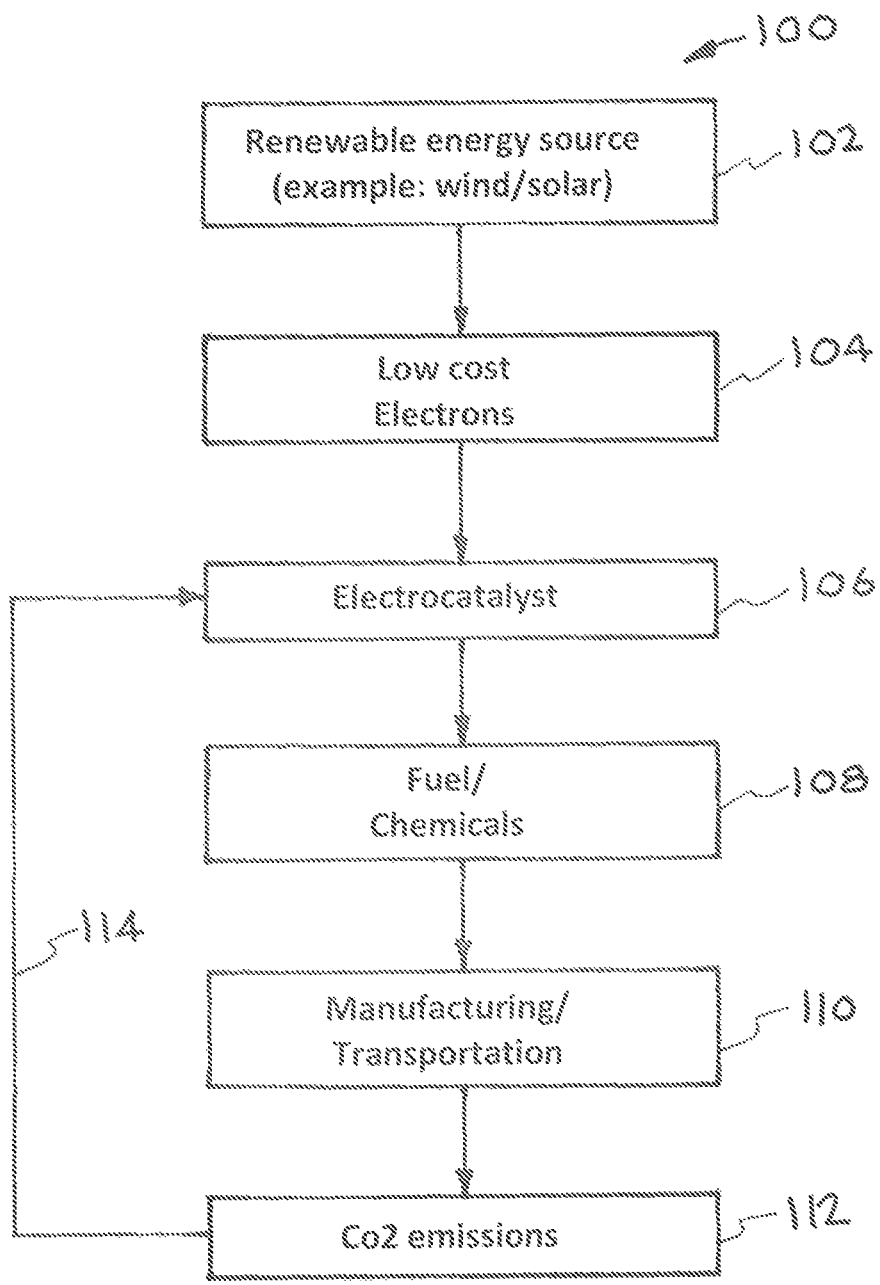
FIG. 1 is a flow chart that illustrates a conceptual model for one or more embodiments of the inventor's apparatus, systems, and methods.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

Referring now to the drawings, and in particular to FIG. 1, a conceptual model for one or more embodiments of the inventor's apparatus, systems, and methods is presented in a flow chart. The model and flow chart are designated generally by the reference numeral 100. The model and flow chart 100 include the components and steps listed below.

102—renewable energy source (example: wind/solar),
104—low cost electrons,
106—electrocatalyst,
108—fuel/chemicals,
110—manufacturing/transportation,
112—$CO_2$ emissions, and
114—recirculation of $CO_2$ from block 112 back to block 106.

The components and steps of the flow chart 100 having been identified and described, the conceptual model will be considered. The inventor's apparatus, systems, and methods provide a scalable, intermediate production module for microbial methanogenesis from $CO_2$. The inventor's apparatus, systems, and methods can also be used in other microbial electrosynthesis including production of other fuels or specialty chemicals, such as hydrogen peroxide or acetate, from $CO_2$.

Renewable energy sources 102 are used to produce low cost electrons 104. An example is the use of solar cells 102 to produce low cost electrons 104. Other sources of low cost electrons can be used. The low cost electrons 104 are used with electrocatalyst 106 to produce fuel and/or chemicals 108. The fuel and/or chemicals 108 are then used in manufacturing and/or transportation 110. The manufacturing and/or transportation 110 produces $CO_2$ emissions 112. The $CO_2$ emissions 112 are recycled back to the electrocatalyst 106.

Figure 2A:
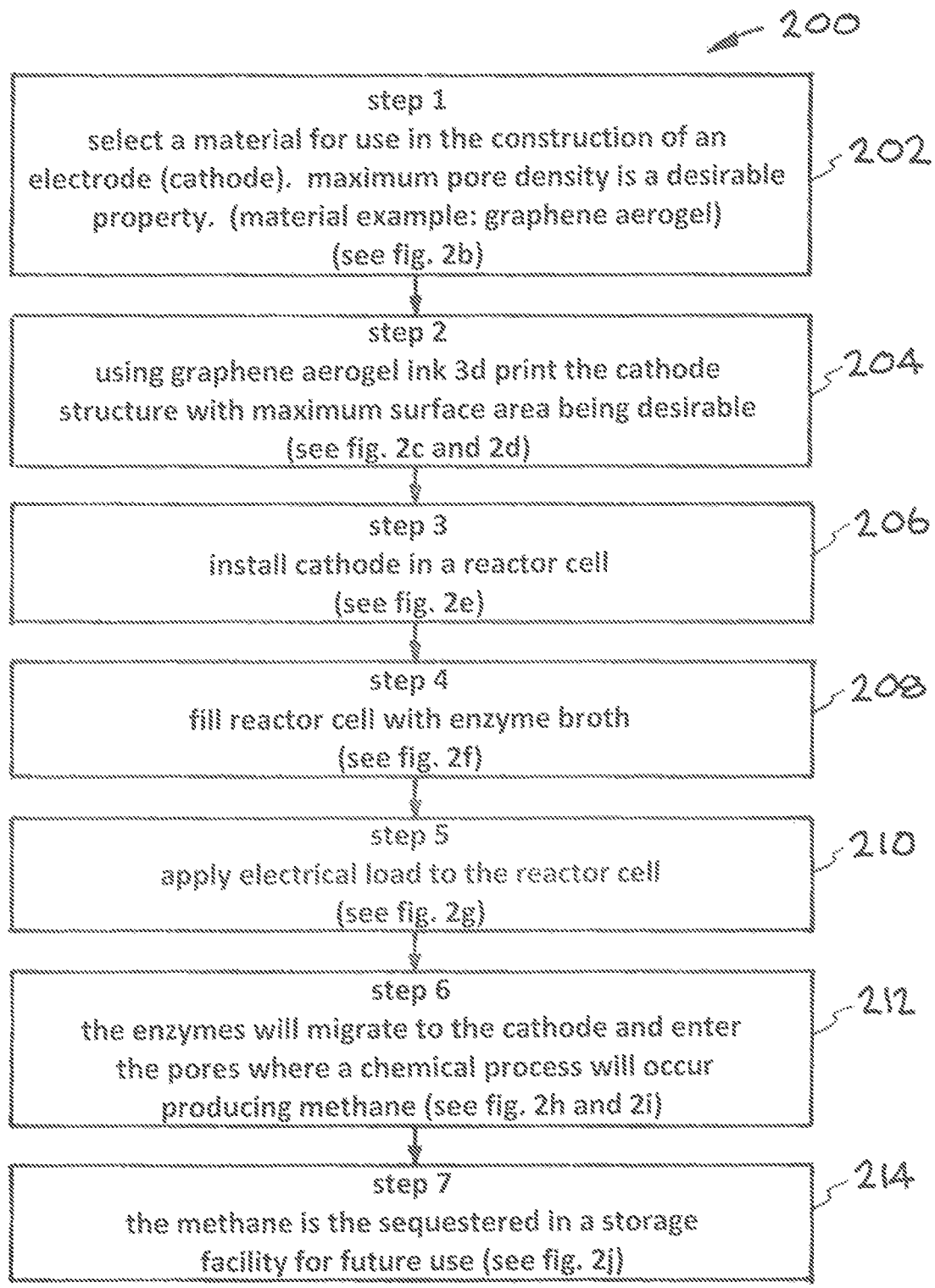
FIG. 2A is a flow chart that illustrates and describes a number of embodiments of the inventor's apparatus, systems, and methods.

Referring now to FIG. 2A through FIG. 2J; numerous embodiments of the inventor's apparatus, systems, and methods are presented. In FIG. 2A a flow chart describes a number of embodiments of the inventor's apparatus, systems, and methods. The embodiments and the flow chart are designated generally by the reference numeral 200. The embodiments and flow chart 200 include the components and steps listed below.

Figure 2B:
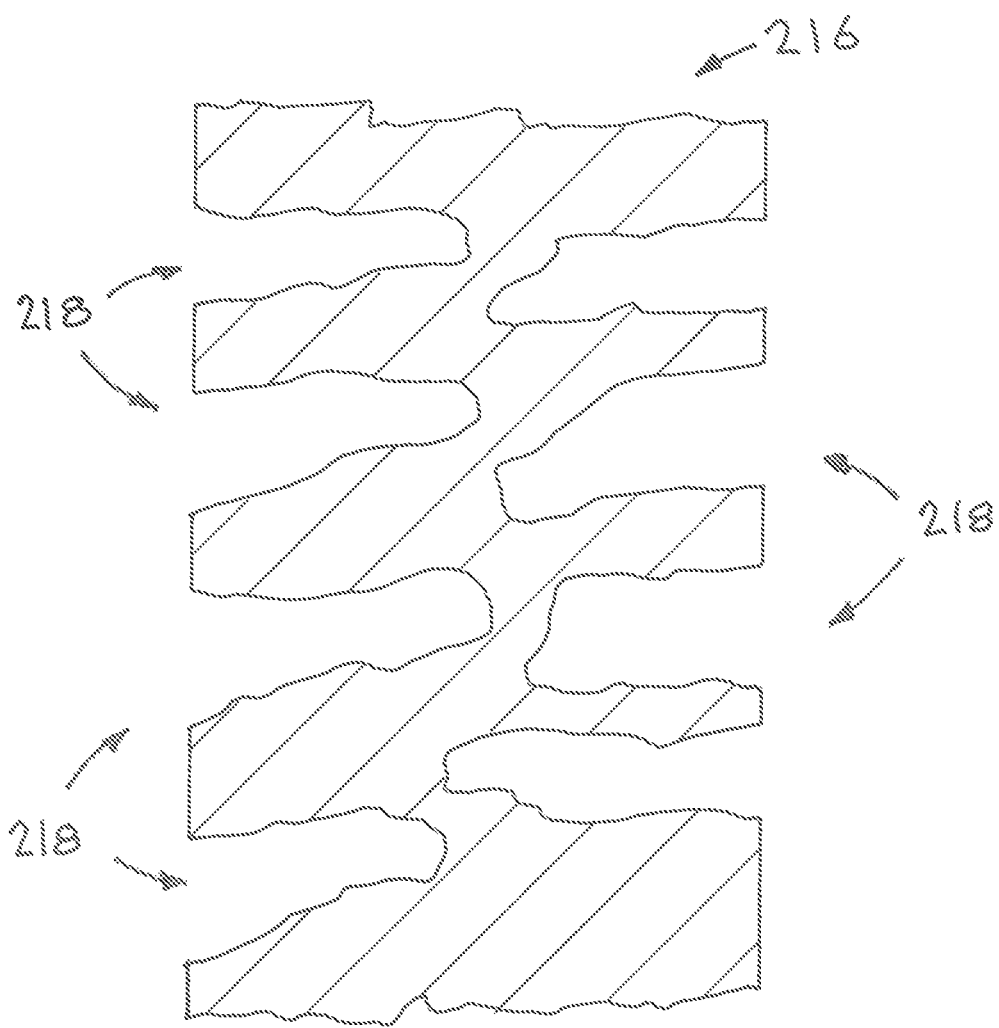
FIG. 2B, is an illustration of a 3D printed cathode electrode of the inventor's apparatus, systems, and methods.
Figure 2C:
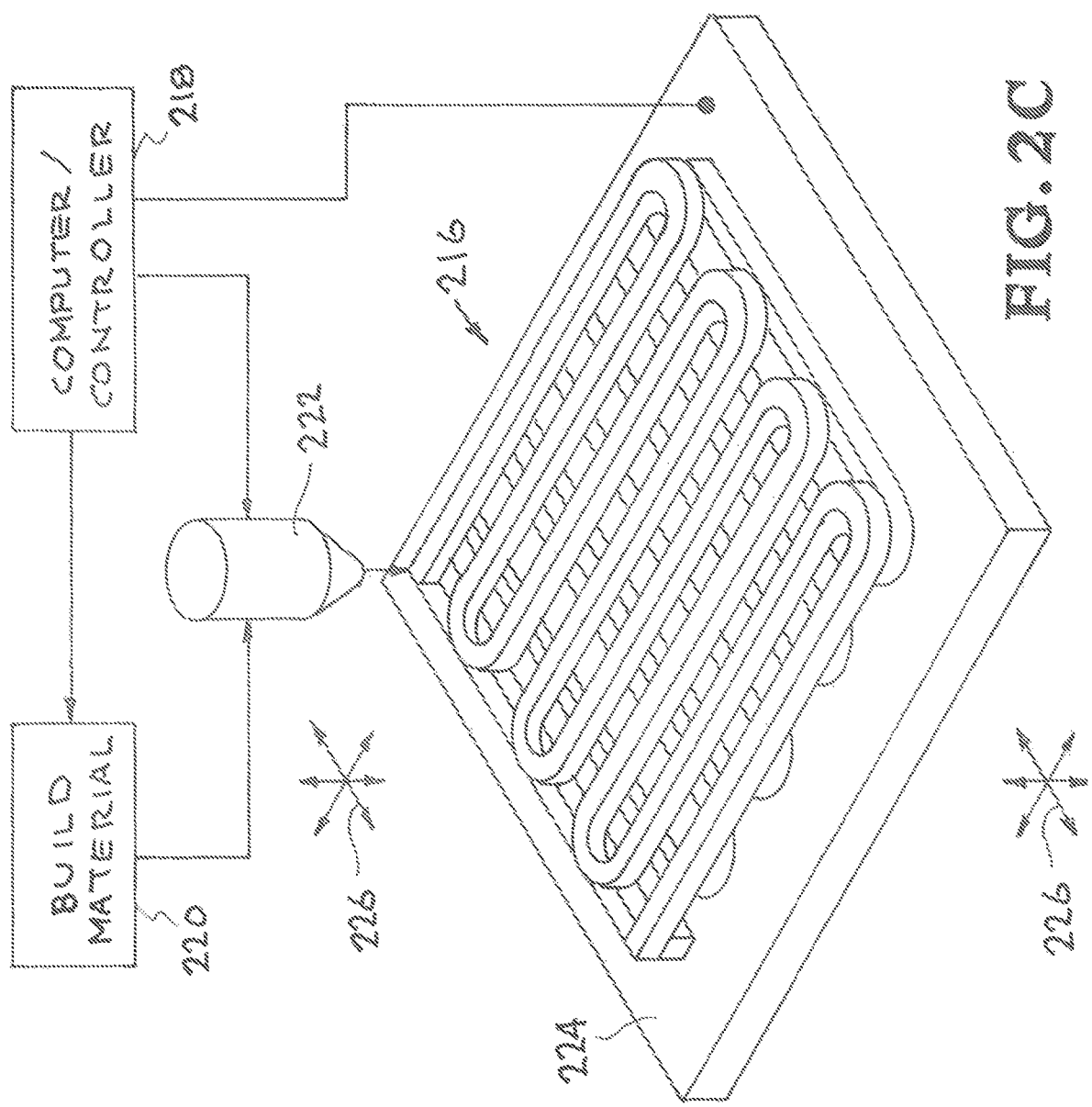
FIG. 2C illustrates an embodiment for 3D printing and otherwise additively manufacturing a cathode electrode of the inventor's apparatus, systems, and methods.
Figure 2D:
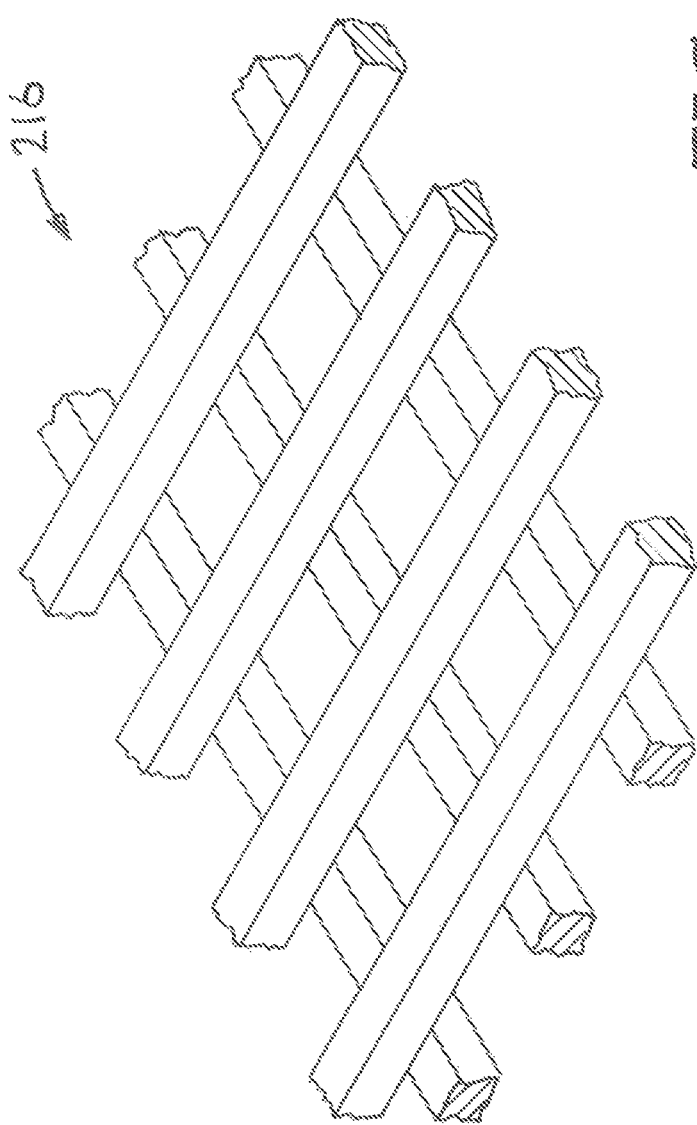
FIG. 2D, illustrates a FIG. 2D a lattice like construction a cathode electrode of the inventor's apparatus, systems, and methods.
Figure 2E:
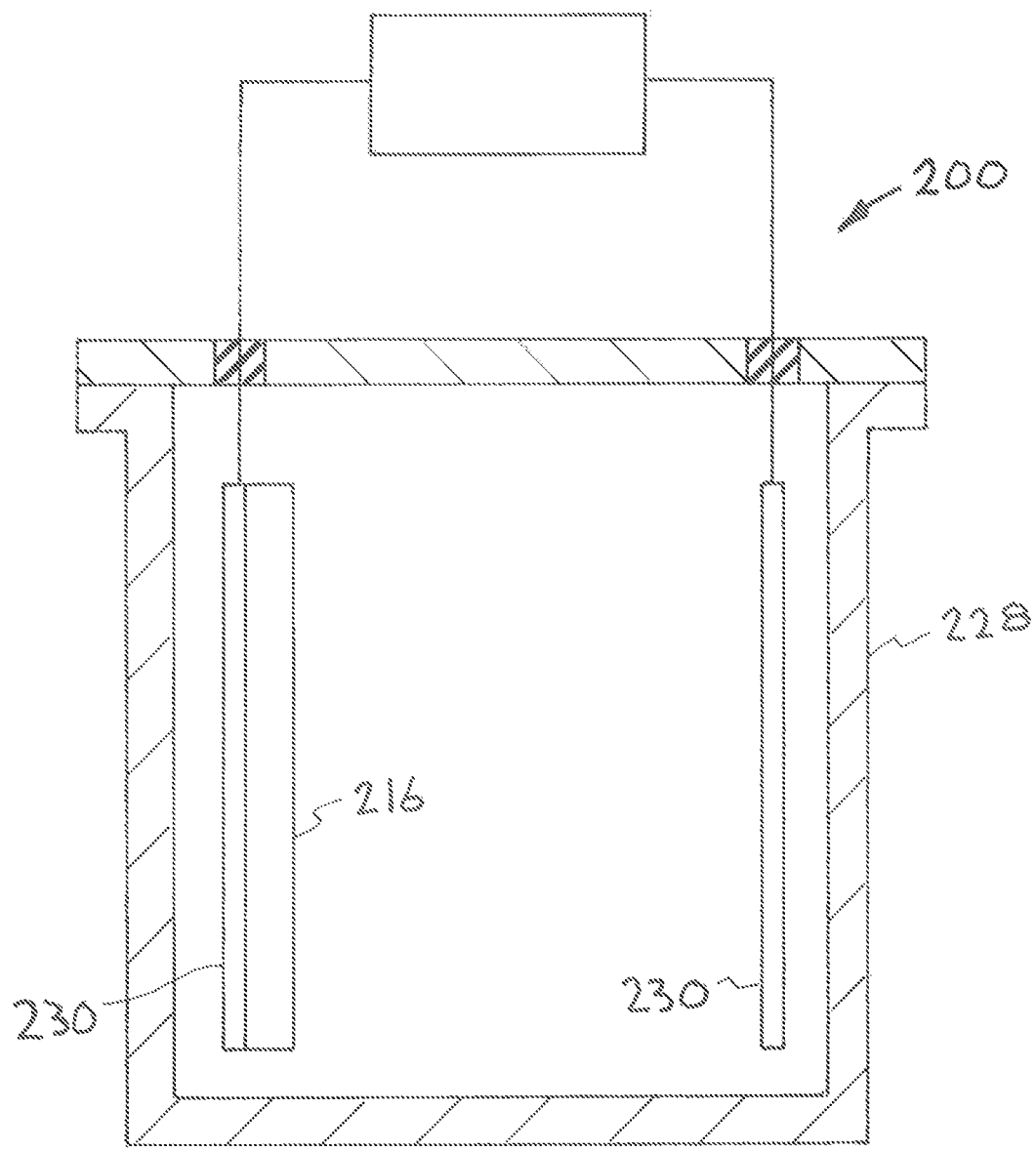
FIG. 2E shows the structural components of an embodiment of the inventors' bioreactor reactor for microbial electromethanogenesis.
Figure 2F:
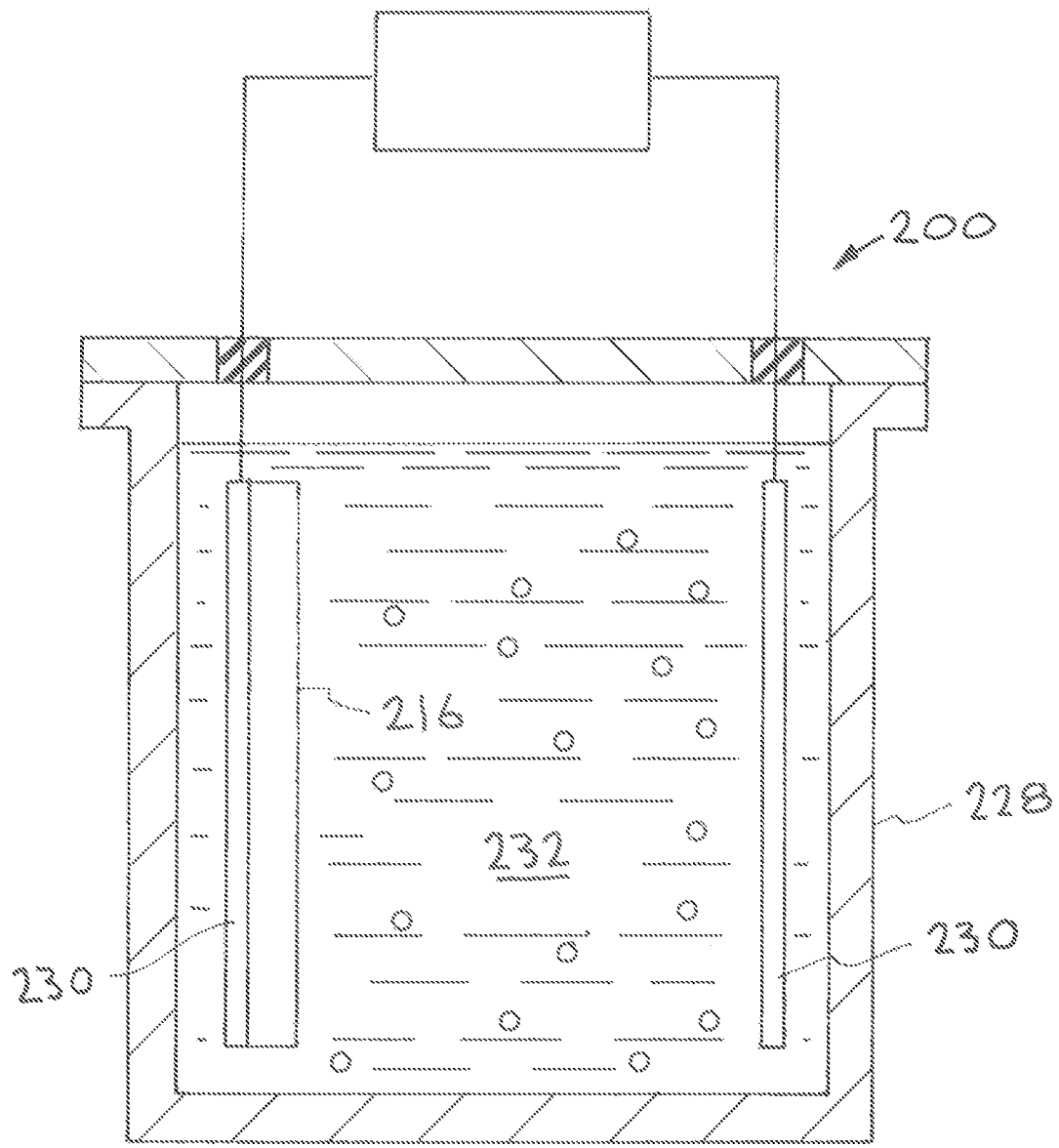
FIG. 2F shows the inventors' bioreactor reactor with the addition of an enzyme broth into the reactor vessel.
Figure 2G:
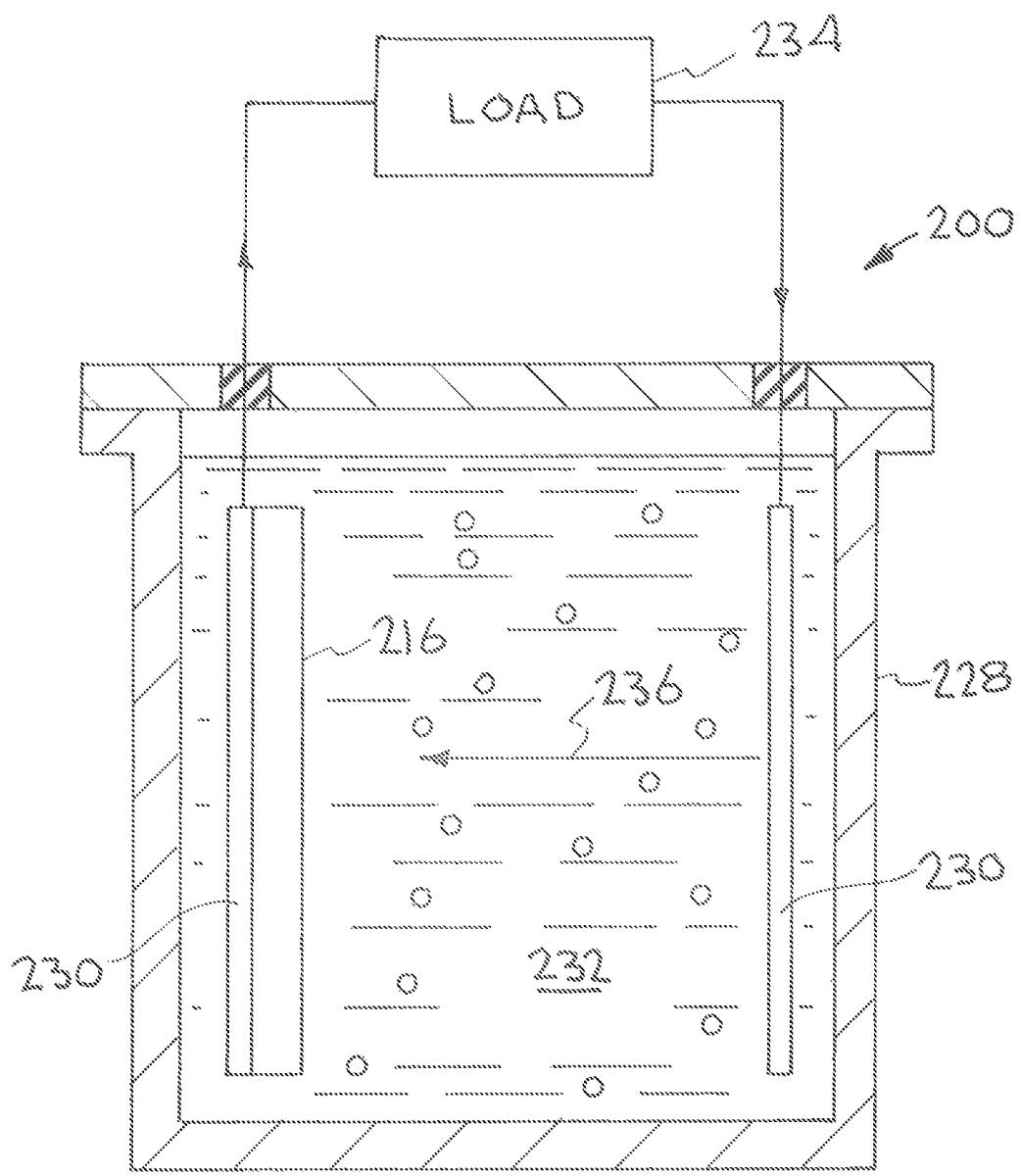
FIG. 2G shows the inventors' bioreactor reactor with the enzyme broth in the reactor vessel 228 and an electrical load 234 connected to the cathode 216 and conductors (cathode electrode conductor & anode electrode conductor) that provides a current with a direction of current.
Figure 2H:
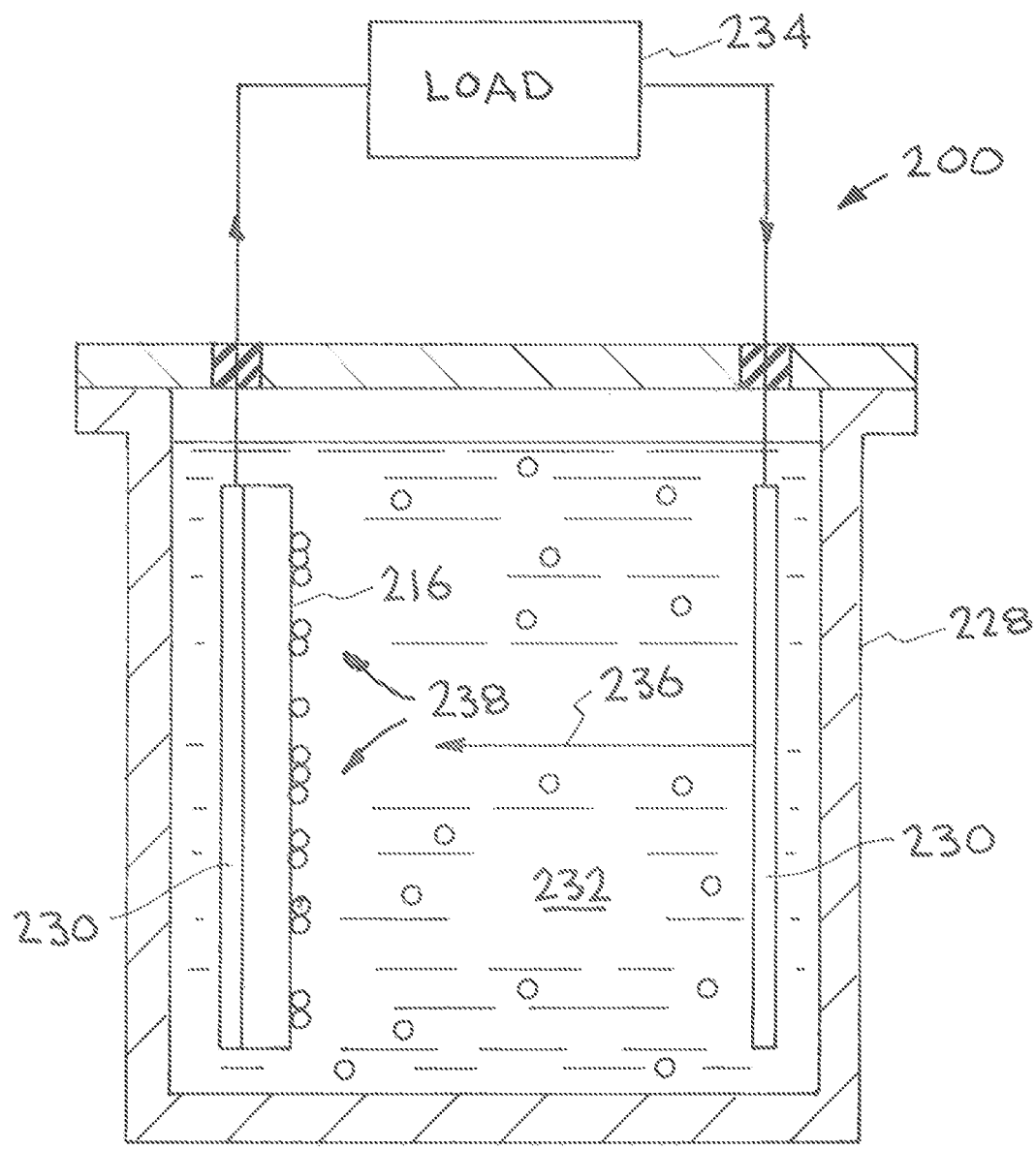
FIG. 2H shows the bioreactor reactor with the enzyme broth in the reactor vessel, an electrical load connected to the cathode and conductors (cathode electrode conductor & anode electrode conductor), and the enzyme broth being drawn to the cathode.
Figure 21:
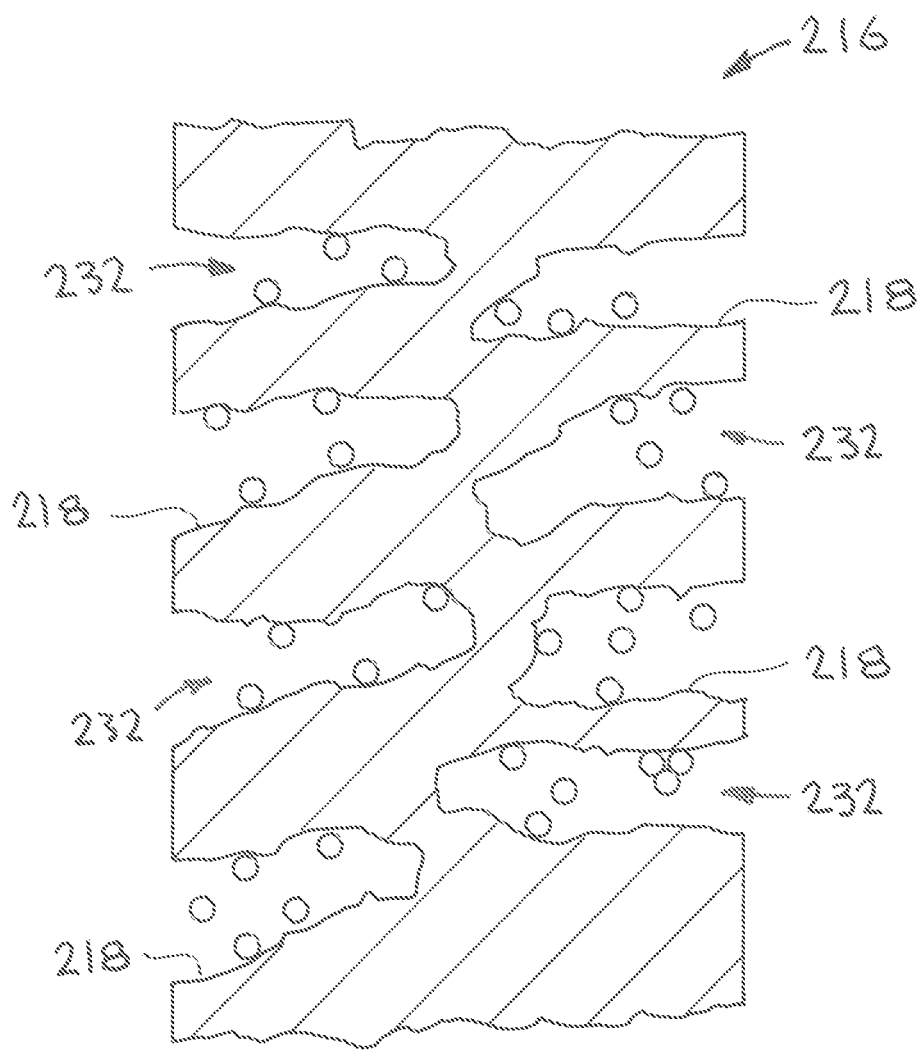

(202) Step 1—Select a material for use in the construction of an electrode (cathode), maximum pore density is a desirable property, (material example: graphene aerogel); this step and component is further illustrated and described in FIG. 2B;

(204) Step 2—Using graphene aerogel ink 3D print the cathode structure with maximum surface area being desirable; this step and component is further illustrated and described in FIG. 2C and FIG. 2D;

(206) Step 3—Install cathode in a reactor cell; this step and component is further illustrated and described in FIG. 2E;

(208) Step 4—Fill reactor cell with enzyme broth; this step and component is further illustrated and described in FIG. 2F;

(210) Step 5—Apply electrical load to the reactor cell; this step and component is further illustrated and described in FIG. 2G;

(212) Step 6—The enzymes will migrate to the cathode and enter the pores where a chemical process will occur; this step and component is further illustrated and described in FIG. 2H and FIG. 2I;

(214) Step 7—The methane is the sequestered in a storage facility for future use; this step and component is further illustrated and described in FIG. 2.

The embodiments and steps of the flow chart 200 having been identified and described, the embodiments of the inventor's apparatus, systems, and methods will be considered. The embodiments of the inventor's apparatus, systems, and methods provide 3D printed electrode materials that have tunable geometry, surface area, and surface chemistry to maximize current density, with adsorbed microbes/enzymes in microbial electromethanogenesis of $CO_2$ to methane in a modular reactor. Volumetric productivity scales with current density, therefore by tuning the surface area and microbe/enzyme adsorption the current density can be empirically studied to achieve an output that cart theoretically achieve volumetric productivity of at least multiple g/L/hr. The use of 3D printable, high porosity resorcinol-formaldehyde aerogel as electrode material also enables unique, scalable reactor geometries and the flexibility of a batch or flow-through reactor design.

Current density scales with productivity because the current results only from electrochemical reactions at the electrode interface at the low (100's of millivolts) potentials applied. To increase current density to a target of 0.1 Amps per m2, which at a target electron capture efficiency of 80% will lead to a very high volumetric productivity of 32 g $CH_4$/L cathode/hour (assuming a surface area of 5×106 m2/m3 and 100% conversion of hydrogen and formate to methane) the electrode interfacial area that is accessible to the enzymes must be maximized. Surface area that is due to pore sizes smaller than the microbes/enzymes/enzyme complexes does not contribute to increase current density. In order to tune the pore size and conductivity of the electrodes, the resorcinol to formaldehyde concentration of the material may be varied during synthesis.

In addition to surface area, the surface chemistry may be tuned to facilitate microbe/enzyme adsorption and beneficial orientation (with the redox active site oriented toward the electrode surface). Controlling surface charge, e.g. by introducing positively charged groups, or introducing transition metals (e.g. Ni nanoparticles) may increase adsorption to electrodes and therefore increase current density and microbe/enzyme stability.

Current density is also controlled by the availability of protons (local pH) at the cathode, since protons are co-reactants in the electrochemical reduction of $CO_2$. Protons are generated by oxidation of water at the anode and are typically supplied through a proton exchange membrane such as Nafion, which also prevents $O_2$ transport to and non-productive reduction at the cathode. The cathode and anode spacing may be varied to optimize proton and $O_2$ transport, and an ion exchange membrane may be printed onto the electrode to prevent $O_2$ transport and separate $O_2$ from the $H_2$ product stream. However, the cathode and anode spacing may be designed such that small bubbles of pure $CO_2$ prevent migration of $O_2$. Unique designs only available to 3D printed or extruded electrode materials, such as coaxial tubes incorporating printed proton exchange membranes, or interdigitated layered electrodes, may be used order to maximize use of the reactor volume. The 3D printed, enzyme-adsorbed electrodes may be used in prototype reactor designs with either batch processing or continuous flow.

The embodiments of the inventor's apparatus, systems, and methods use 3D printed high surface area electrode-based reactors with adsorbed enzymes for charge transfer to overcome the limitations of microbial electromethanogenesis. The inventor's apparatus, systems, and methods have three unique aspects that are designed to increase charge transfer efficiency and reactor volumetric productivity:

First, this is the first use of graphene aerogels for microbial electromethanogenesis, which allows the current density to be maximized due to the ability to control material pore size (and thus biologically accessible surface area) over 4 orders of magnitude (1 nm to 10 μm) and conductivity from 1 to 100's of S/cm.

Second, the inventor's apparatus, systems, and methods use adsorbed enzymes to mediate charge transfer rather than whole microbial cultures. The use of enzymes to mediate charge transfer can increase current density, since nanometer scale enzymes can access more electrode surface area than significantly larger micron scale whole microbes. Furthermore, using enzymes rather than microbes for the critical charge transfer step allows a wider range of process conditions, e.g. temperatures and pH, which can be used to increase catalytic activity and $CO_2$ solubility. Separating the charge transfer from the methanogenesis step to a chemical intermediate production step also allows a wider range of microbial species that can be used for methanogenesis; processes for microbial methane production from syngas have been optimized and established for industrial biogas production.

Third, 3D printing these reactors maximizes volumetric productivity by both optimally utilizing 3D space and reducing diffusion limitations. Furthermore, 3D printed reactors allow for modular and flow-through designs, positioning the technology for scale-up and commercialization.

Referring now FIG. 2B, an embodiment of an electrode of the inventor's apparatus, systems, and methods is illustrated. The electrode is designated generally by the reference numeral 116. The electrode 116 is a 3D printed cathode electrode constructed of materials that are compatible with enzymes that are adsorbed or attached to the electrode. The materials for the construction of the cathode electrode 116 provide maximum pore density. The materials can be carbon with high porosity. For example, the materials can be carbon aerogel with high porosity. An example is graphene aerogel. In a preferred embodiment the materials are resorcinol-formaldehyde aerogel with high porosity. The 3D printed cathode electrode has a tunable geometry, surface area, and surface chemistry to maximize current density in microbial electromethanogenesis of $CO_2$ to methane in a modular reactor. As shown in FIG. 2B the cathode electrode 216 includes pores 218. The pores 218 are sub-micron to micron scale pores that provide high surface area.

Referring now FIG. 2C, an embodiment that provides apparatus, systems, and methods for 3D printing and otherwise additively manufacturing a cathode electrode 216 of the inventor's apparatus, systems, and methods is illustrated.

As illustrated in FIG. 2C, extruded build material 220 is deposited on a build platform 224 by print head 222. The extruded build material 220 is composed of materials that have tunable geometry, surface area, and surface chemistry to maximize current density in microbial electromethanogenesis of $CO_2$ to methane in a modular reactor. The print head 222 has a nozzle for extruding the build material 220 onto the build platform 224. Movement of the print head 222 is controlled by computer controller 218 which provides freedom of movement along all axes as indicated by the arrows 226. The specifications of the cathode electrode 216 product to be created by the system is fed to the computer controller 218 with the widely used numerical control programming language G-Code. The computer controller 218 uses the instructions to move the print head 222 through a series of movements along the surface 224 forming the cathode electrode 216 product. The materials for the construction of the cathode electrode 216 are materials that provide maximum pore density. An example is graphene aerogel. In a preferred embodiment the materials are resorcinol-formaldehyde aerogel with high porosity. The cathode electrode 216 includes pores that are sub-micron to micron scale pores that provide high surface area.

Referring now FIG. 2D, an embodiment of a 3D printed cathode electrode 216 of the inventor's apparatus, systems, and methods is illustrated. The electrode 216 is a 3D printed cathode electrode constructed of materials that are compatible with microbes or enzymes that are adsorbed or attached to the electrode. The materials for the construction of the cathode electrode 216 provide maximum pore density. The materials can be carbon with high porosity. For example, the materials can be carbon aerogel with high porosity. An example is graphene aerogel. In a preferred embodiment the materials are resorcinol-formaldehyde aerogel with high porosity. The 3D printed cathode electrode has a tunable geometry, surface area, and surface chemistry to maximize current density in microbial electromethanogenesis of $CO_2$ to methane in a modular reactor. As shown in FIG. 2B the cathode electrode 216 includes pores 218. The pores 218 are sub-micron to micron scale pores that provide high surface area. As illustrated in FIG. 2D, a lattice like construction gives a large surface area. The materials for the construction of the cathode electrode 216 provide maximum pore density.

Referring now to FIG. 2E, structural components of an embodiment of the inventors' bioreactor reactor for microbial electromethanogenesis is illustrated. The bioreactor reactor is designated generally by the reference numeral 200. The bioreactor reactor 200 includes the components listed below.
  cathode 216,
  reactor vessel 228,
  conductors (cathode electrode conductor & anode electrode conductor) 230.

The reactor vessel 238 houses cathode 216 and conductors (cathode electrode conductor & anode electrode conductor) 230. The cathode 216 is a 3D printed cathode electrode constructed of materials that will adsorb microbes or enzymes and that has tunable geometry, surface area, and surface chemistry to maximize current density in microbial electromethanogenesis of $CO_2$ to methane in the reactor 200. The materials used in the construction of the cathode electrode 116 provide maximum pore density. An example is graphene aerogel. The cathode electrode 116 includes pores that are sub-micron to micron scale pores that provide high surface area.

Referring now to FIG. 2F, the bioreactor reactor 200 is shown with the addition of an enzyme broth into the reactor vessel 228. The enzyme broth is represented by open circles 232. The reactor vessel 238 houses cathode 216, conductors (cathode electrode conductor & anode electrode conductor) 230, and enzyme broth 232.

Referring now to FIG. 2G, the bioreactor reactor 200 is shown with the enzyme broth 232 in the reactor vessel 228 and an electrical load 234 connected to the cathode 216 and conductors (cathode electrode conductor & anode electrode conductor) 230. The load 234 provides a current with a direction of current 236 illustrated in FIG. 2G.

Referring now to FIG. 2H, the bioreactor reactor 200 is shown with the enzyme broth 232 in the reactor vessel 228, an electrical load 234 connected to the cathode 216 and conductors (cathode electrode conductor & anode electrode conductor) 230, and the enzyme broth 232 being drawn to the cathode 216. The current 236 draws the enzyme broth 232 to the cathode 216.

Referring now FIG. 2I, details of the cathode electrode 216 are illustrated. The electrode 216 is a 3D printed cathode electrode constructed of materials that have tunable geometry, surface area, and surface chemistry to maximize current density in microbial electromethanogenesis of $CO_2$ to methane with adsorbed enzymes 232 in a modular reactor. The materials for the construction of the cathode electrode 216 provide maximum pore density. The cathode electrode 216 includes pores 218. The pores 218 are submicron to micron scale pores that provide high surface area. The enzymes 232 are linked to the cathode electrode 216 in the pores 218. The materials can be carbon with high porosity. For example, the materials can be carbon aerogel with high porosity. An example is graphene aerogel. In a preferred embodiment the materials are resorcinol-formaldehyde aerogel with high porosity. The 3D printed cathode electrode has a tunable geometry, surface area, and surface chemistry to maximize current density in microbial electromethanogenesis of $CO_2$ to methane.

Figure 2J:
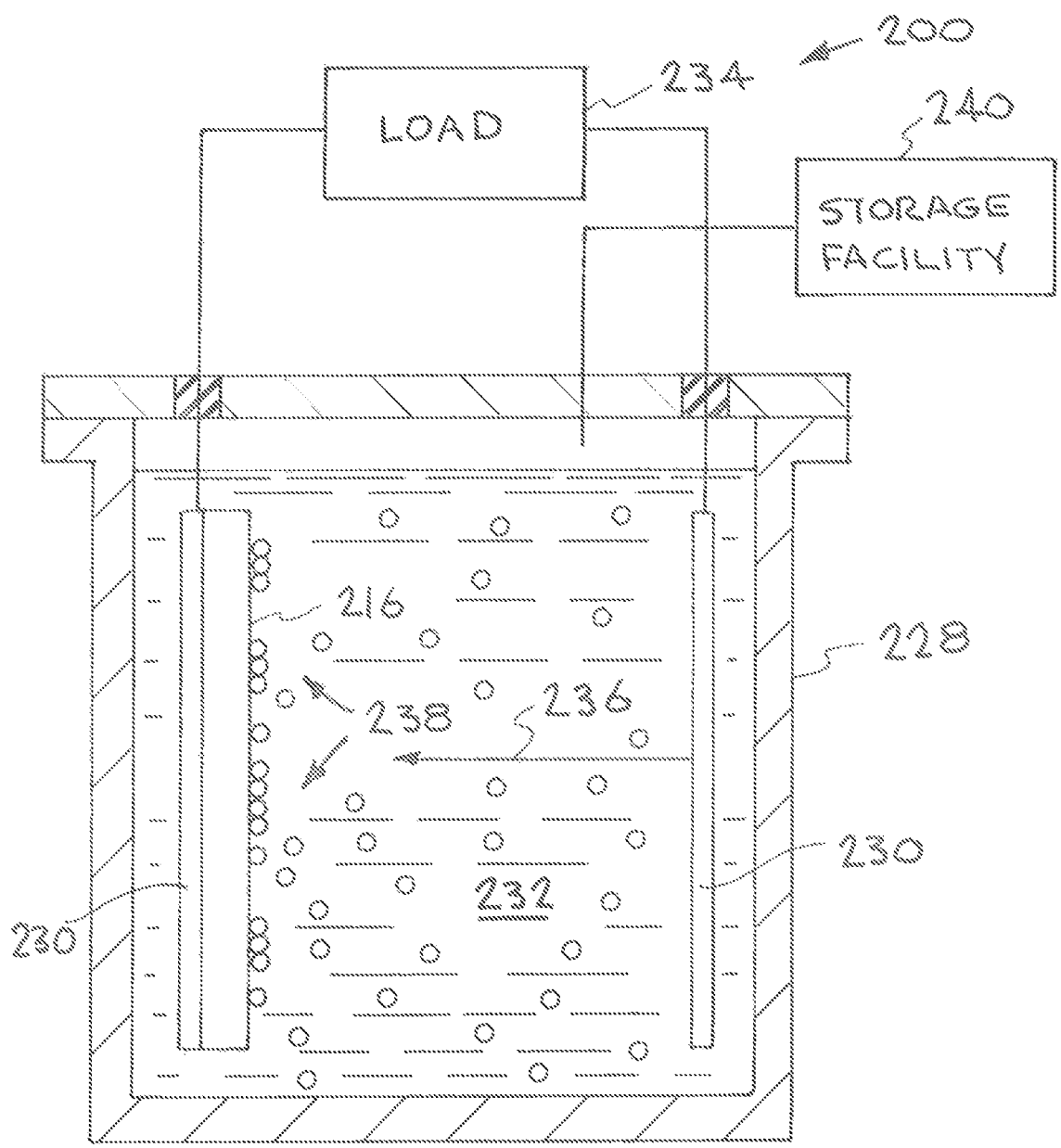
FIG. 2J shows the inventors' bioreactor reactor with the enzyme broth in the reactor vessel, an electrical load connected to the cathode and conductors (cathode electrode conductor & anode electrode conductor), wherein the enzyme broth is drawn to the cathode and a storage facility is connected to the reactor.

Referring now to FIG. 2J, the bioreactor reactor 200 is shown with the enzyme broth 232 in the reactor vessel 228, an electrical load 234 connected to the cathode 216 and conductors (cathode electrode conductor & anode electrode conductor) 230, the enzyme broth 232 drawn to the cathode 216, and storage facility 240. The bioreactor reactor 200 produce methane and the methane is collected in the storage facility 240.

Figure 2K:
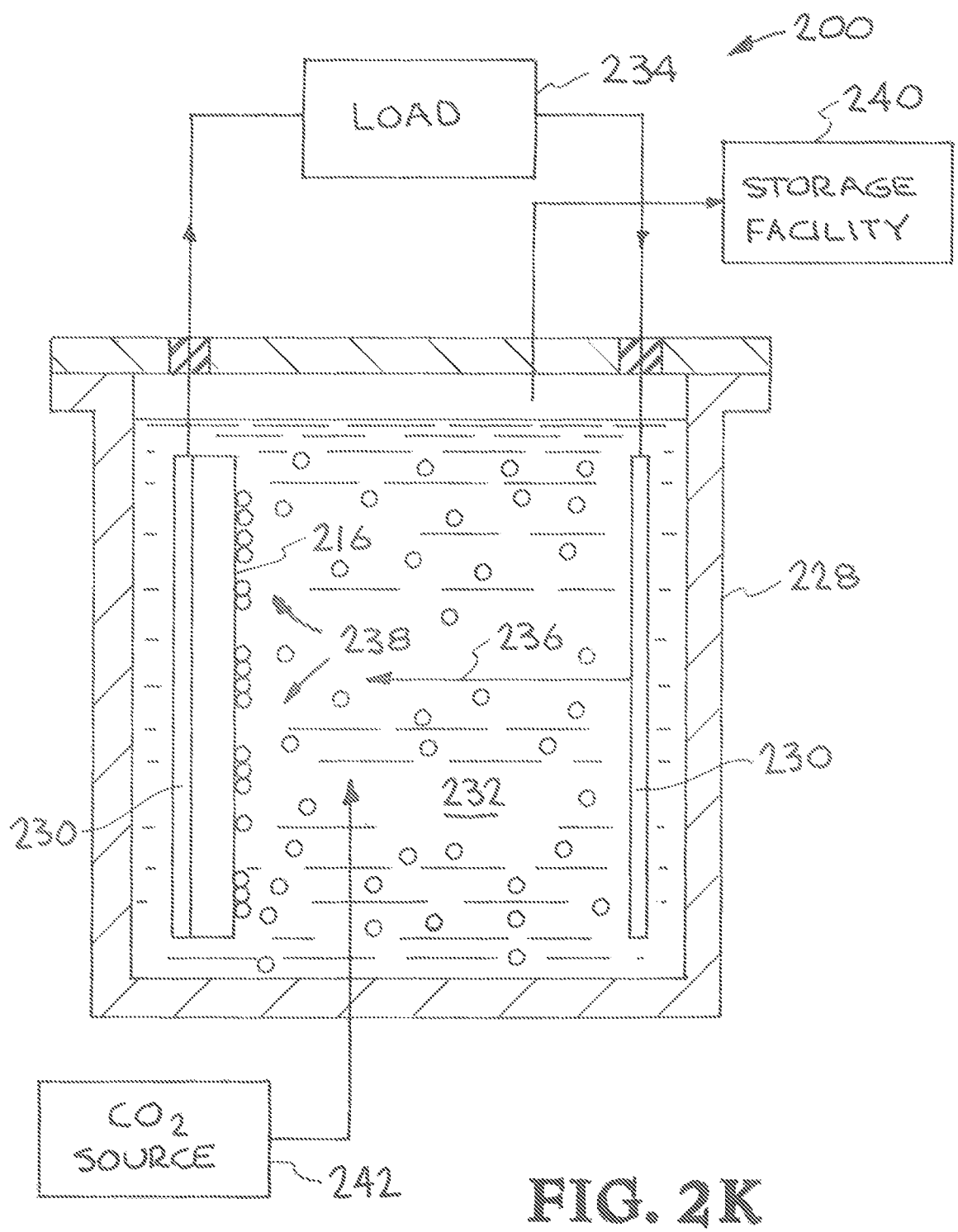
FIG. 2K shows the inventors' bioreactor reactor with the enzymes in the reactor vessel, an electrical load connected to the cathode and conductors (cathode electrode conductor & anode electrode conductor), wherein the enzymes are drawn to the cathode, a storage facility, and a system for introducing carbon dioxide into the reactor vessel.

Referring now to FIG. 2K, the bioreactor reactor 200 is shown with the enzymes 232 in the reactor vessel 228, an electrical load 234 connected to the cathode 216 and conductors (cathode electrode conductor & anode electrode conductor) 230, storage facility 240, and $CO_2$ 242 being introduced into the enclosure 228. The $CO_2$ and the enzymes 232 produce methane in the bioreactor reactor 200 and the methane is collected in the storage facility 240.

Referring again to FIGS. 2E through 2K, details and the operation of the inventors' bioreactor reactor 200 for microbial electromethanogenesis will be described. The bioreactor reactor includes the components listed below.
  electrodes (cathode electrode & anode electrode) 230,
  reactor vessel 228,
  cathode 216,
  enzyme broth (the enzymes are represented by open circles) 232,
  load 234,
  direction of current 236,
  migrating enzymes 238, and
  storage facility 240.

We are entering an era where energy from photovoltaics and other renewable sources is abundant and inexpensive during peak production periods. Therefore, technologies that can store this abundant energy long term are highly desired. Recently, it was discovered that certain microbes are capable of converting electrical current and carbon dioxide into fuels such as methane. The net reaction for electromethanogenesis is similar to that of photosynthesis, when solar energy is used as a source of electrons:

$$CO_2 + 8H^+ + 8e^- \rightarrow CH_4 + 2H_2O \quad \text{[Equation 1]}$$

However, if the electrons are harvested from photovoltaic panels, the artificial photosynthesis afforded by microbial electromethanogenesis (ME) is about 100 times more efficient than terrestrial bioenergy crops at harvesting solar energy. Additionally, ME does not require arable land, and can lead to a pure product stream, circumventing the downstream processing challenges currently encountered in converting dedicated bioenergy crops to fuels. The electron capture efficiency in ME is typically around 90%, and the overall energy efficiency from $CO_2$ to methane around 80%. While microbial electrosynthesis is being pursued for conversion of electrical energy and $CO_2$ to fuels or chemicals such as hydrogen peroxide or acetate, the production of methane has specific advantages: Methane can serve as an energy storage medium that can be stored or transported using mature technologies and immediately integrated into existing infrastructure. Natural gas power plants emit fewer pollutants and are more efficient than coal-fired power plants. Furthermore, in this scheme, for each methane molecule produced, a $CO_2$ molecule is consumed, reducing the climate impacts of burning natural gas.

Both biological and materials/reactor design challenges must be overcome to commercialize the ME process. The inventors will focus on breakthroughs in reactor design that the inventors can achieve given recent advances in the additive manufacturing of high surface area carbon materials. The fundamentals of ME, specifically the electron transfer mechanism between the cathode and the microbe, are not well understood and are an active area of research. However, optimizing this interface, and thus the charge transfer, between the material and the microbe, and scaling the materials for optimal use of the bioreactor volume are critical toward creating a practical, scalable reactor. Because of this lack of understanding, research into optimizing the materials interface, i.e. the surface chemistry to enhance charge transfer, must be empirical.

Other desired aspects of the reactor design can be anticipated from assessments of the path to commercialization of bioenergy crops and microbial fuel cells: first, to minimize capital costs, high volumetric production rates of at least multiple g/L/hr are necessary. High volumetric productivity, several orders of magnitude higher than this target, can theoretically be achieved with the high current density, measured in $A/m^2$, high coulombic efficiency (utilization of this current by the microbe or adsorbed enzymes), and the high accessible electrode surface area materials synthesized at LLNL, up to $500 \times 10^6$ $m^2/m^3$. Additionally, a decade of research on microbial fuel cells (which generate current from the biological oxidation of organics in wastewater) teaches us that electrode materials are desired which have high accessible surface area, are not prone to biofouling, and show high conductivity, and high stability. The inventors also learn from the lessons of microbial fuel cells in terms of challenges that have been encountered in scale-up and industrial implementation: "the main difficulty is not an intrinsic loss of power at scales but maintaining reactor geometry relative to electrode configurations and densities as larger reactors are built . . . ". This observation implies that scale-up can be achieved if modular designs are implemented and proven at smaller scales. These requirements of 1) high surface area 2) highly conductive electrodes built into 3) modular reactors which optimally deliver high current densities in three-dimensional space can be met using LLNL 3D printed electrode materials. In fact, LLNL routinely 3D prints electrode materials which have comparable conductivity, but 100 fold higher surface areas than what has been used previously in ME. The ability to print these materials into limitless geometries and modular reactors adds another key benefit: scalable reactors can be constructed which potentially do not require membranes, which reduce or eliminate proton and $CO_2$ diffusion limitations, which optimize use of three dimensional space, and thus the volumetric productivity of the reactor, and finally which enable continuous production of products in a flow-through design.

The present invention is further described and illustrated by examples of apparatus, systems, and methods constructed in accordance with the present invention. Various changes and modifications of these examples will be apparent to those skilled in the art from the description of the examples and by practice of the invention. The scope of the invention is not intended to be limited to the particular examples disclosed and the invention covers all modifications, equivalents, and alternatives falling within the spirit and scope of the invention as defined by the claims.

3D Printing of ARF (Acid-Catalyzed Resorcinol-Formaldehyde) Aerogel

A suspension of 3 g of water, 3.4 g of formaldehyde (F) (37% solution) and 6 wt % of cellulose was prepared by ultra-sonication for 24 h. After sonication and prior printing, 2.46 g of resorcinol (R) and 88 µL of acetic acid (catalyst (C)) were added to the suspension. This combination of R/F molar ratio of 1:2 and R/C molar ratio of 1:15, yielded a RF mass ratio of 42 wt %. After the addition of resorcinol, the 6 wt % of cellulose drops to 4 wt % in the overall suspension. The overall suspension is mixed for 5 min at 2000 rpm in a Thinky mixture until a through mixing of resorcinol with formaldehyde/water/cellulose suspension was obtained. However, for direct ink writing a thixotropic ink is necessary with elastic stiffness such that the extruded beads from the nozzle can span easily. To achieve the required stiffness in the inks, 9 wt % of Fumed silica was mixed to the suspension and was then loaded to a syringe barrel for printing. The ink is then loaded into a syringe barrel and centrifuged for a minute at 4000 rpm to remove air bubbles, after which the ink is extruded through a micro nozzle (600 µm or 250 µm diameter) to pattern 3D structures. The patterns were printed on a glass substrate coated with PTFE spray. Simple cubic lattices with multiple orthogonal layers of parallel cylindrical rods were printed alternately. The diameter of the cylindrical rods equals the diameter of nozzle and the center-to-center rod spacing of 1.2 mm (for 600 µm nozzle) and 0.8 mm (250 µm nozzle) were respectively used. A total of 10 layers were stacked on the structure such that each layer has a z spacing of 0.3 mm. In order to avoid cracking due to evaporation of water, drops of iso-octane (2,2,4-trimethyl-pentane) was added onto the printed structure frequently. The printed parts on the glass substrate is carefully placed in a container with iso-octane and sealed tightly to avoid evaporation of the solvent and are placed in the oven at 80° C. for 72 h for gelation. Once gelled, the aqueous solvent (water in this case) is removed by soaking the sample in an acetone bath for 3 days. Note that the solvent needs to be exchanged every 24 h. This step is crucial as the following procedure of super critical drying is carried out with $CO_2$. The samples are then super critically dried in liquid $CO_2$ at a critical temperature of 55° C. and at a pressure range of 1200-1400 psi.

Carbonization and Activation of 3D Printed ARF Aerogel

This process involves carbonizing the supercritically dried 3D printed ARF organic gel to form carbon aerogels. The aerogels were subjected to a heat treatment process where the samples were heated in a tube furnace under nitrogen atmosphere at 1050° C. for 3 h with a heating and cooling rate of 2° C./min. The carbonized 3D printed CAs were then etched with hydrofluoric acid to remove fumed silica. The etched parts were again subjected to a three-day solvent (acetone) exchange followed by super critical drying. For activation, the samples are now exposed to an oxidizing atmosphere at 950° C.

Figure 3:
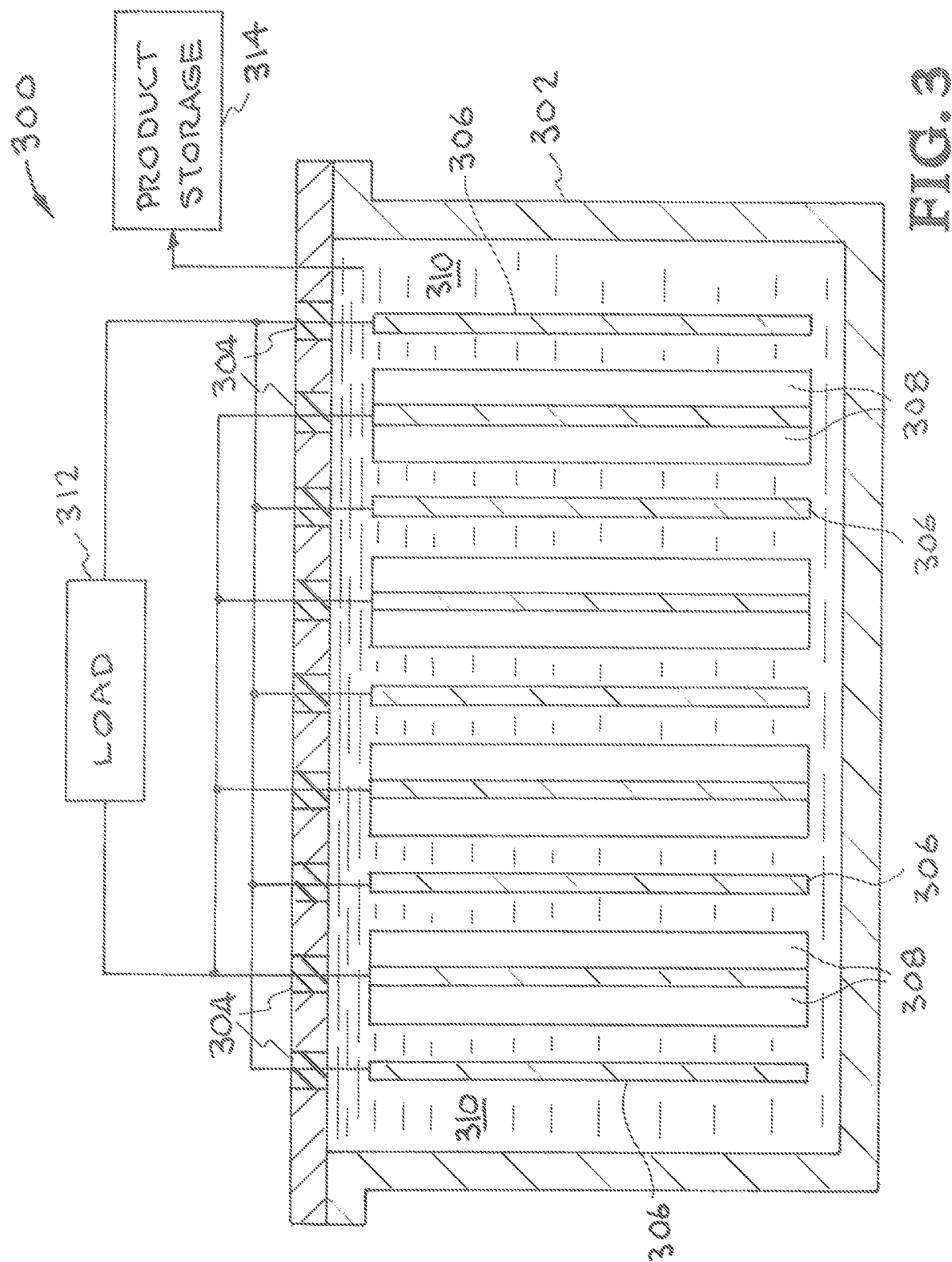
FIG. 3 illustrates an embodiment of the inventors' bioreactor reactor that includes a 3D cathode reactor array for microbial electromethanogenesis.

Referring now to FIG. 3, structural components of a 3D cathode reactor array for microbial electromethanogenesis is illustrated. The 3D cathode reactor array is designated generally by the reference numeral 300. The 3D cathode reactor array 300 includes the components listed below.

reactor housing (non-conducting) 302,
electrical isolators 304,
conductors (anode) 306,
3D cathodes 308,
enzyme broth 310.
load 312, and
product storage 314.

The reactor housing 302 houses electrical isolators 304, conductors (anode) 306, and 3D cathodes 308, and enzyme broth 310. The 3D cathodes 308 are 3D printed cathode electrodes constructed of materials that will adsorbed enzymes and that has tunable geometry, surface area, and surface chemistry to maximize current density in microbial electromethanogenesis of $CO_2$ to methane in the reactor 300. The materials used in the construction of the 3D cathodes 308 provide maximum pore density. An example is graphene aerogel. The 3D cathodes 308 include pores that are submicron to micron scale pores that provide high surface area. The reactor 300 provides ganged 3D cathodes 308 to increase the output of the reactor 300.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. An apparatus for generating energy and storing the energy for subsequent use, comprising:
   an electromethanogenesis reactor,
   an anode electrode conductor in said reactor,
   a cathode electrode conductor in said reactor wherein said cathode electrode conductor is a 3D printed cathode electrode conductor with cubic lattices having ten orthogonal layers of parallel cylindrical rods,
   submicron to micron scale pores in said cathode electrode conductor,
   electromethanogenesis enzymes in said submicron to micron scale pores in said cathode electrode conductor,
   electromethanogenesis microbes in said submicron to micron scale pores in said cathode electrode conductor,
   a CO2 source for introducing carbon dioxide into said reactor,
   an electrical load connected to said anode electrode conductor and said second cathode electrode conductor wherein fuel gas is produced in said reactor, and
   a storage system for storing said fuel gas for subsequent use.

2. The apparatus for generating energy and storing the energy for subsequent use of claim 1 wherein said cathode electrode conductor is a graphene aerogel cathode electrode conductor.

3. An apparatus for generating energy and storing the energy for subsequent use, comprising:
   an electromethanogenesis reactor,
   an anode electrode conductor in said reactor,
   a cathode electrode conductor in said reactor wherein said cathode electrode conductor is a resorcinol-formaldehyde aerogel cathode electrode conductor with cubic lattices having ten orthogonal layers of parallel cylindrical rods,
   submicron to micron scale pores in said cathode electrode conductor, electromethanogenesis enzymes in said submicron to micron scale pores in said cathode electrode conductor,
electromethanogenesis microbes in said submicron to micron scale pores in said cathode electrode conductor,
a $CO_2$ source for introducing carbon dioxide into said reactor,
an electrical load connected to said anode electrode conductor and said cathode electrode conductor wherein fuel gas is produced in said reactor, and
a storage system for storing said fuel gas for subsequent use.

4. The apparatus for generating energy and storing the energy for subsequent use of claim 3 wherein said cathode electrode conductor is a 3D printed cathode electrode conductor having a thickness that is greater than the thickness of standard electrodes.

5. The apparatus for generating energy and storing the energy for subsequent use of claim 3 wherein said cathode electrode conductor is a 3D printed cathode electrode conductor having a surface and pores that extend from said surface into said 3D printed cathode electrode conductor.

6. The apparatus for generating energy and storing the energy for subsequent use of claim 3 wherein said electrical load provides current density in said cathode electrode conductor and wherein said submicron to micron scale pores in said cathode electrode conductor, said electromethanogenesis enzymes, and said electromethanogenesis microbes are selected to provide maximum current density in said cathode electrode conductor.

7. The apparatus for generating energy and storing the energy for subsequent use of claim 3 wherein said electromethanogenesis enzymes in said submicron to micron scale pores in said cathode electrode conductor, said electromethanogenesis microbes in said submicron to micron scale pores in said cathode electrode conductor, said $CO_2$ source for introducing carbon dioxide into said reactor, and said electrical load for applying a voltage to said anode electrode conductor and said cathode electrode conductor produces methane gas in said reactor.

8. A reactor apparatus for electromethanogenesis of carbon dioxide to methane, comprising:
an electromethanogenesis reactor housing,
an anode electrode conductor in said electromethanogenesis reactor housing;
a cathode electrode conductor in said electromethanogenesis reactor housing, said cathode electrode conductor having submicron to micron scale pores wherein said cathode electrode conductor is a resorcinol-formaldehyde aerogel cathode electrode conductor with cubic lattices having ten orthogonal layers of parallel cylindrical rods;
electromethanogenesis enzymes in said submicron to micron scale pores in said cathode electrode conductor,
electromethanogenesis microbes in said submicron to micron scale pores in said cathode electrode conductor,
a s $CO_2$ source for introducing carbon dioxide into said electromethanogenesis reactor housing; and
an electrical load connected to said anode electrode conductor and said cathode electrode conductor wherein methane is produced in said electromethanogenesis reactor housing.

9. The reactor apparatus for electromethanogenesis of carbon dioxide to methane of claim 8 wherein said cathode electrode conductor is a 3D printed cathode electrode conductor having a thickness that is greater than the thickness of standard electrodes.

10. The reactor apparatus for electromethanogenesis of carbon dioxide to methane of claim 8 wherein said cathode electrode conductor is a 3D printed cathode electrode conductor having a surface and pores that extend from said surface into said 3D printed cathode electrode conductor.

11. The reactor apparatus for electromethanogenesis of carbon dioxide to methane of claim 8 wherein said cathode electrode conductor is a resorcinol-formaldehyde aerogel cathode electrode conductor.

12. A method of electromethanogenesis of carbon dioxide to methane, comprising the steps of:
providing an electromethanogenesis reactor housing,
providing an anode electrode conductor in said electromethanogenesis reactor housing;
providing a cathode electrode conductor in said electromethanogenesis reactor housing, said cathode electrode conductor having submicron to micron scale pores wherein said cathode electrode conductor is a resorcinol-formaldehyde aerogel cathode electrode conductor with cubic lattices having ten orthogonal layers of parallel cylindrical rods;
providing electromethanogenesis enzymes in said submicron to micron scale pores in said cathode electrode conductor,
providing electromethanogenesis microbes in said submicron to micron scale pores in said cathode electrode conductor,
providing a $CO_2$ source for introducing carbon dioxide into said electromethanogenesis reactor housing; and
providing an electrical load connected to said anode electrode conductor and said cathode electrode conductor wherein methane is produced in said electromethanogenesis reactor housing.

13. The method of electromethanogenesis of carbon dioxide to methane of claim 12 further comprising the step of selecting said electromethanogenesis enzymes and said electromethanogenesis microbes to provide maximum current density in said cathode electrode conductor.

14. The method of electromethanogenesis of carbon dioxide to methane of claim 12 wherein said step of providing a cathode electrode conductor in said electromethanogenesis reactor housing, said cathode electrode conductor having submicron to micron scale pores comprises providing a 3D printed cathode electrode conductor having a thickness that is greater than the thickness of standard electrodes.

* * * * *